United States Patent [19]

Wilhelm

[11] Patent Number: Plant 6,493

[45] Date of Patent: Dec. 27, 1988

[54] "JOE MELLO" RED RASPBERRY

[75] Inventor: Stephen Wilhelm, Watsonville, Calif.

[73] Assignee: Sweetbriar Co., Watsonville, Calif.

[21] Appl. No.: 16,231

[22] Filed: Feb. 19, 1987

[51] Int. Cl.[4] ..... A01H 5/00

[52] U.S. Cl. ..... Plt./46

[58] Field of Search ..... Plt./46

*Primary Examiner*—James R. Feyrer

*Attorney, Agent, or Firm*—Limbach, Limbach & Sutton

[57] ABSTRACT

A primocane bearing cultivar of red raspberry designated "Joe Mello" and as a cross of the unpatented cultivar "Reiter 323" and a Canadian cultivar known as "Chilcotin" is disclosed. The cultivar exhibits minutely spiny primocanes with predominately ternately pinnate leaves, minutely prickled pedicels and bright glossy red berries.

2 Drawing Sheets

BACKGROUND OF THE NEW CULTIVAR

This invention relates to a new and distinct cultivar of red raspberry designated as "Joe Mello", originated in 1981 as a cross of the unpatented cultivar known as "Reiter 323" and a Canadian cultivar known as "Chilcotin", and fruited first and was selected at Cassin Ranch of Reiter Companies, Watsonville, Calif. in 1983.

The botanical classification is *Rubus idaeus* L. cv. "Joe Mello". The commercial classification is Primocane Bearing Red Raspberry.

Asexual propagation of the newly discovered raspberry cultivar has been made at Cassin Ranch of Reiter Companies, Watsonville, Calif. by dormant cane divisions, root cuttings and root shoot cuttings. Cane divisions, root cuttings and root shoot cuttings so taken have consistently produced raspberries that have the new and distinct characteristics hereinafter described. "Joe Mello" has been tested extensively at various Reiter Company facilities located in Pajaro Valley, a Central Coastal berry growing region of the state of California, under strict control.

DESCRIPTION OF THE DRAWING

Typical plant, flower and fruit characteristics are presented in the accompanying drawing in which:

FIGS. 1 and 2 illustrate primocane flower and fruit trusses;

FIG. 3 illustrates primary, secondary and tertiary fruit, the torus or receptacle apical leaf and flower bud characteristics; and FIG. 4 illustrates mature vegetative leaves.

DESCRIPTION OF THE NEW PLANT

The characteristics of this new raspberry plant as described in detail below, were observed upon its discovery and subsequently through its test period. Plant vigor, foliage and fruit color, foliage and fruit size, blooming periods and yield of fruit may vary somewhat with environmental conditions such as winter cold, day length, light intensity, temperature, rainfall, soil moisture and fertility and the presence of diseases. The color description is given by designation "H" for hue and "L" for lightness in color chart references designated "LCC" for Limited Color Cascade, Munsell Color, Baltimore, Md. Plant descriptive terminology follows that of William J. Stearn, "Botanical Latin; History, Grammar, Syntax, Terminology and Vocabulary", Hafner, N.Y., 1966.

Novel Characteristics— (Summary)

The new cultivar herein named "Joe Mello" has displayed novel characteristics as follows:

(a) Primocane bearing from July 15 to November 30 accounting for approximately $\frac{2}{3}$ of the total annual crop.

(b) Significant production for commercialization 6 months after planting dormant canes.

(c) Primocanes minutely spiny, spines dehisce on overwintering canes.

(d) Apical leaflets of nature ternately compound leaves of primocanes sporadically lobed, basal leaflets truncate, near sessile, tending to slight downward cupping.

(e) Pedicels minutely prickled; commonly arise as morphological doubles even triples from same bud on fruiting lateral.

(f) Mature berry, symmetrical, druplets uniform in size; develop evenly, tight fitting. Torus short tapering, yielding readily to picking pressure.

(g) Berry color, bright glossy red; little evidence of white powdery bloom; slight tendency to darken during shipping. Excellent to moderate flavor.

(h) Plant, foliage and fruit shows high resistance but not immunity to strains of the powdery mildew fungus presently extant.

Plant Habit

The new plant described herein is a medium in vegetative vigor. Grown in hedgrows, primocanes are erect and sturdy, attaining a height of five to six feet (150–180 cm.) within six months of growth when planted in December or January as dormant roots or dormant canes taken from cold storage. For canes, a planting distance of approximately 18 inches (45 cm.) in rows spaced 88 inches (200 cm.) apart was used throughout testing periods; for roots the same row spacing was used.

Primocanes

Primocanes attaining a height of five to six feet (150–180 cm.) have diameters ranging on the average from $\frac{3}{8}$ to $\frac{3}{4}$ in. (8–15 cm.), measured at 12 inches (30 cm.) above the ground. Primocanes throughout most their length are light green, "LCC 5.7 GY, 8.9/4.2 becoming somewhat reddish in areas directly exposed to sun, and minutely spiny. As observed under a 10× hand lens, spines appear reddish brown. Spines dehisce as canes age and during overwatering.

Floricanes

Canes which have not borne fruit during the first year of growth but have gradually passed into dormancy during the fall, and overwinter and bear fruit in the spring of the following year, are the floricanes. Floricanes are white, to light brown, nearly smooth, and bear fruit on laterals (racemes) which have grown from dormant overwintering buds. Dormant buds situated at any position along floricane axes may initiate fruiting laterals. Dormant buds situated at or closest to the apex of the floricane especially if pruned—which is our commercial practice—tend to initiate spring growth more readily than those farther from the apex.

Floricane intermodal distance of this new cultivar, in contrast to "Heritage", also a primocane bearer, are commonly one to two inches (2.5 to 5 cm.) which gives the new plant a distinct, sturdy compactness and a potential for greater productivity per unit of floricane cane bearing length than Heritage. In contrast, cane intermodal distances of "Heritage" are commonly as much as 3 to 4 inches (7.5 to 10 cm.).

Leaves

Mature fully developed primocane leaves are predominantly ternately pinnate; petioles of the two basal leaflets, that is, those arising opposite each other on the leaf petiole, may be reduced to the extent that leaflets appear sessile. The terminal or central leaflet is petiolulate and may range in shape for ovate to cordate (heart shaped); it sporadically becomes variously lobed. Basal leaflets are ovate, acute at the tips, generally truncate at the base; they may cup downward along the main rib, but the cupping is rarely more than slight and contrast sharply to the deep downward cupping of leaflets of "Sweetbriar", U.S. Plant Pat. No. 4,486).

Mature primocane leaflets, excluding those developing apically within the flower truss are medium to large in size. Blades of the terminal leaflets are usually 3.5 to 4.5 inches (9–11 cm.) long, 2–4 inches (5–10 cm.) wide, or wider if lobed. Petiolules are usually 1.0 to 1.5 inches (2.5 to 3.75 cm.) in length. Blades of basal leaflets range from 3 to 4 inches (7.5 to 10 cm.) in length, 2 to 2.5 inches (5 to 6.5 cm.) in width at their widest distance. Opposite leaflets of the compound leaf vary only slightly in dimensions. Petiolules of basal leaflets are much reduced and as seen from the undersurface of the leaf appear as extensions of the midrid of the leaflet. Leaflets are irregularly serrate; serrations increase in prominence toward the tops of the leaflets. The leaf petiole is generally close to 2–2½ inches (5.0 to 6.5 cm.) in length; sipules are small and needlelike, rarely attaining 10 mm. in length. The overall plant color is generally slightly darker green than "Sweetbriar" (U.S. Plant Pat. No. 4,486). Upper surface color of recently mature primocane leaves are viewed in morning sunlight, with light falling directly on the leaf, is "LCC" 6.1 GY, 3.2/5.8.

Flower and Fruit Bearing Truss

The truss of fruit bearing laterals (racemes) on which the summer and fall crops (July 15–November) are borne, develop at the apices of the first formed primocanes. The laterals arise singly from primocane modes, which modes also bear the normal trifoliate green leaves. Laterals are flexuous and bear both simple sanceolate-ovate green leaves and the fruit bearing pedicels. Leaves borne on laterals are smaller, measuring only about one-third the length of leaflets of the normal trifoliate leaf. Stipules or bracts subtending pedicels are needle-shaped, and measure approximately one-fourth of an inch (5–6 mm.) in length. Pedicels are minutely prickled. Pedicels frequently appear as morphological doubles and even triples from the same lateral node. Where more than one pedicel arises from the same node, the secondary and tertiary are subordinate to the primary pedicel as shown in the accompanying illustration; they bear fruit that is correspondingly smaller than that ripens later by two or three weeks.

Fruit Architecture and Color

Ripe fruit as shown in the accompanying illustration are rounded, to conical, symmetrical and compact. Druplets are uniform in size, and tight fitting resulting in a compact, symmetrical, firm berry. The berry readily separates from the short tapering torus when picked. Color is bright, crisp red "LCC" 5.5R, 2.9/11.6. The color holds well for several days of cold storage, after which a slight tendency to darken may be evident. The darkening, if it occurs, is only slight and far less intense than that of "Willamette"; if affects neither the qualities of berry firmness nor flavor. Druplets of this outstanding, novel raspberry resist collapsing after harvest. Berries have shown only a slight predisposition to develop on their sun exposed side the bloom or dusty powdery coating which strongly characterize fruit appearance of "Willamette" and "Amity" grown in the Pajaro Valley. Fruit have also resisted infection by the fungus causing the powdery mildew disease.

Fruit Size and Weight

July, August and early September produced primocane berries whether from plants originating at planting from canes or roots, average a little more than 4 gm. fresh weight each, requiring 55 to 60 to fill an 8 oz. basket. As the season progressed, berry size and weight decreased slightly. Berries produced between September 15 and November 1 averaged about 3 grams each, requiring 75–80 to fill a basket. November produced berries averaged 2.6 gms., requiring 85–90 to fill a basket.

Primocane "Yields"

Planted as described above, first primocane flower buds appear around mid-May, open flowers and immature fruit early to mid June, ripe fruit early to mid July. First picking of the 1985 commercial test block, grown on the Sheehy Ranch of Reiter Companies of Watsonville, was during the week of July 15; peak production occurred between August 19 and September 7. Significant production continued until the end of November. First year primocane yields—July through November—of the novel cultivar of this invention was equivalent to slightly above 3500 six pound trays per acre; each tray consisted of twelve 8 oz. [225–230 gram] baskets of freshly picked berries. Planted as described above, but with root pieces taken from cold storage instead of dormant canes, primocane growth and fruit production lagged behind that of the plants developed from canes by two to three weeks and ended the season with slightly above 2,600 six pound trays per acre, or approximately 1,000 trays per acre less than that of the canes.

Floricane or Spring Production

Spring fruit production occurs on floricanes. After pruning to a height of 4 to 4½ feet (120–135 cm.) dormant buds of this novel cultivar, herein delineated, initiate new growth which becomes the fruiting laterals. This burst of new spring growth typically occurs between the middle and end of February, in the Pajaro Valley of California. It may be delayed following unusually warm winters. Floricane fruiting laterals are long and flexuous, and bear trifoliate leaves somewhat distinct in morphology from leaves of primocanes, and flower buds primarily in apical leaf axils. Lateral internodes may range from 2.0–3.0 inches (5.0–7.5 cm.), leaf petioles 2.0–3.0 inches (5.0–7.5 cm.); petiolules about 1.0 inch (2.5 cm.). Basal leaflets are ovate, serrate, 1.0–1.5 inches (2.5–3.75 cm.) at their widest dimension, 2.0–3.5 inches (5.0–8.75 cm.) in length, sessile. Petiolules, if present, are extremely short. Apical leaflets are ovate to obovate, serrate, 1.5–2.0 inches (3.75–5.0 cm.), in width, 1.5–3.0 inches (3.75–7.5 cm.) in length, often truncate.

Flowering typically begins early in March; fruit production, from about April 15 through the end of June. Spring production coincides pretty well in timing with that of "Sweetbriar" (U.S. Plant Pat. No. 4,486).

Spring produced berries of "Joe Mello", herein described, are of highest quality and may amount to a total of 1,500 to 2,000 12 basket trays per acre.

Thus, total annual production under the ideal culture maintained by Reiter Companies of Watsonville during the long fruiting season, if free from excessive rain, may reach 5,000 to 6,000 12 baskets trays per acre, or 30,000 to 36,000 pounds of marketed berries.

The cultivar characteristic of this novel plant described above were observed during the first fruiting cycle of primocane bearing following winter planting, and the first cycle of floricane bearing following passage of the first dormancy (winter) period. All observations were made in the Watsonville area near the Pacific Ocean. Planting stock was maintained as free from virus, bacterial, fungus, nematode incited diseases and insect pests as possible. Evaluations were made in fields which had bee preplant fumigated with a mixture of methyl bromide and chloropicrin at dosages known to control major resident root infecting fungus and nematode species. Raspberry root systems were healthy, extensive and vigorous. Fields were always weed-free and watered by a metered drip irrigation system.

I claim:

1. The new and distinct cultivar of red raspberry herein described and illustrated and identified by the characteristics enumerated above.

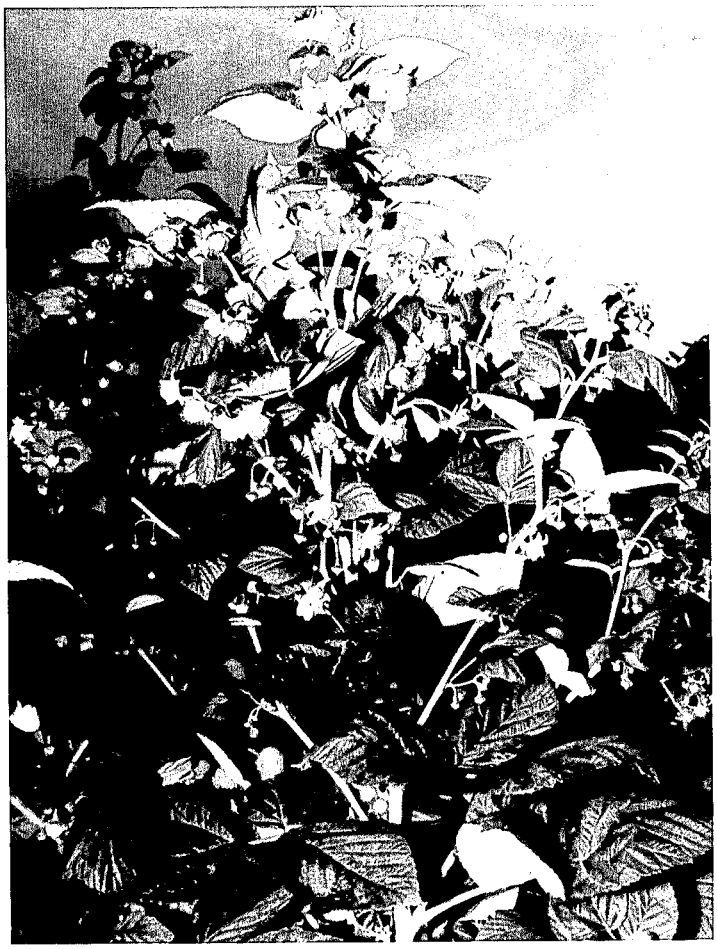
FIG. 1.
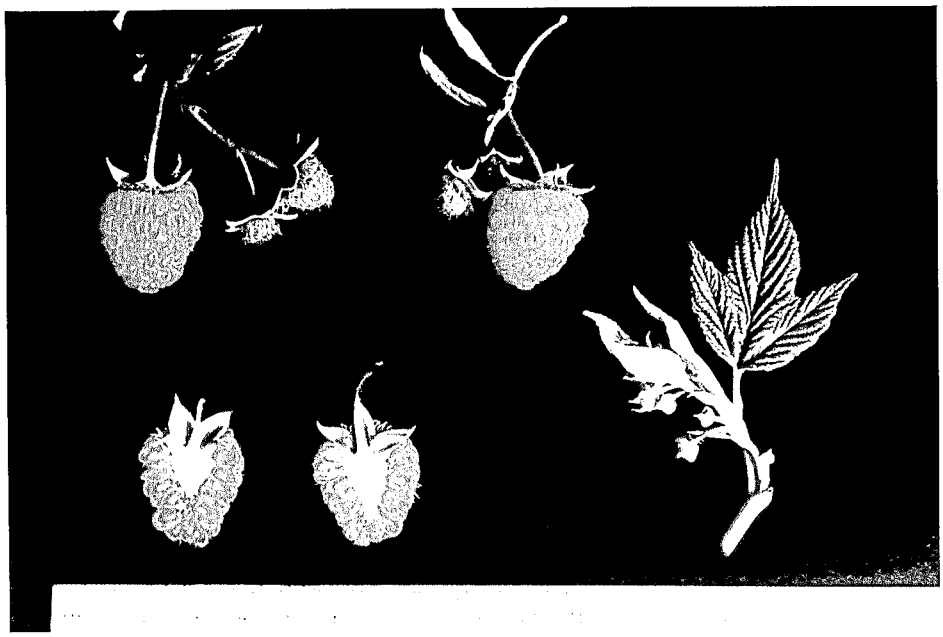

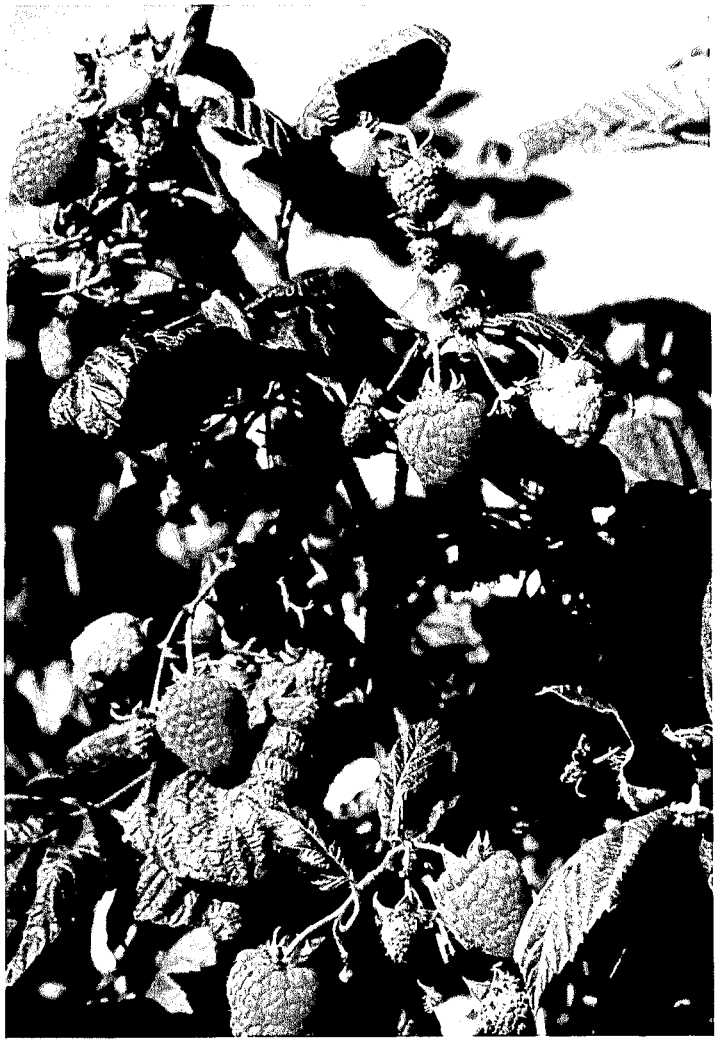
FIG._2.
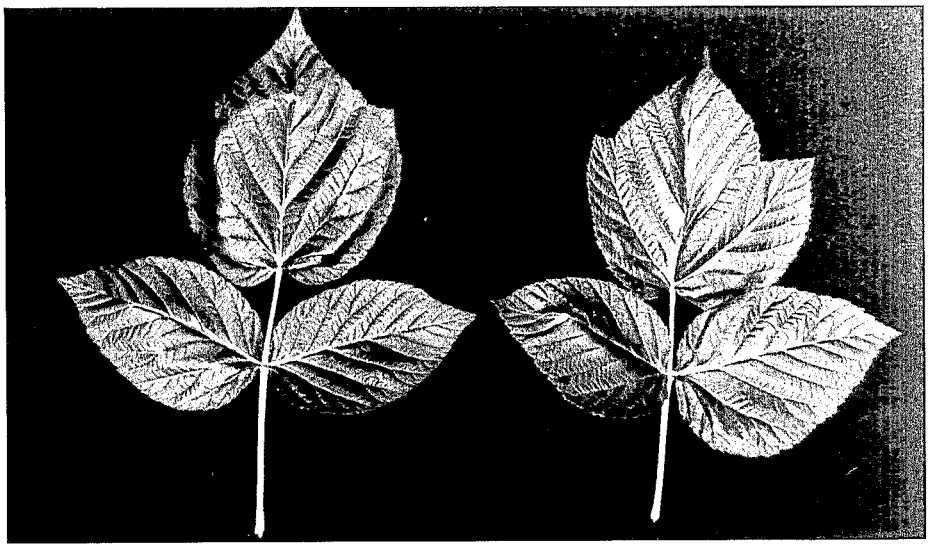

* * * * *